United States Patent [19]

Portugall et al.

[11] 4,293,435
[45] Oct. 6, 1981

[54] LIQUID-CRYSTALLINE POLYMER PHASE HAVING A CHOLESTERIC STRUCTURE, PROCESSES FOR ITS PREPARATION AND ITS USE

[75] Inventors: Michael Portugall, Eltville; Heino Finkelmann, Clausthal-Zellerfeld; Helmut Ringsdorf, Mainz-Gonsenheim, all of Fed. Rep. of Germany

[73] Assignee: BASF Aktiengesellschaft, Fed. Rep. of Germany

[21] Appl. No.: 58,943

[22] Filed: Jul. 19, 1979

[30] Foreign Application Priority Data

Jul. 20, 1978 [DE] Fed. Rep. of Germany ....... 2831909

[51] Int. Cl.$^3$ .......................... C09K 3/34; G02F 1/13
[52] U.S. Cl. .......................... 252/299.01; 252/299.65; 252/299.66; 252/299.67; 252/299.7; 73/356; 428/1; 526/320; 526/321; 526/325; 526/326; 350/330; 350/352
[58] Field of Search .................. 252/299, 408; 73/356; 260/901; 526/320, 321, 325, 326; 428/1; 350/330, 352

[56] References Cited

U.S. PATENT DOCUMENTS

| | | | |
|---|---|---|---|
| 4,001,137 | 1/1977 | Steinstrasser | 252/299 |
| 4,065,489 | 12/1977 | Steinstrasser et al. | 252/299 |
| 4,070,912 | 1/1978 | McNaughtan | 252/299 |
| 4,140,016 | 2/1979 | Fergason | 252/299 |
| 4,149,413 | 4/1979 | Gray et al. | 252/299 |
| 4,195,916 | 4/1980 | Coates et al. | 252/299 |

FOREIGN PATENT DOCUMENTS 2736424 2/1978 Fed. Rep. of Germany ...... 252/299

OTHER PUBLICATIONS

Finkelmann, H. et al., ACS Polymer Preprints, vol. 19, No. 2, pp. 183-189 (Aug. 1978).
Wendorff, J. et al., ACS Polymer Preprints, vol. 18, No. 2, pp. 5-8 (Aug. 1977).
Clouch, S. et al., ACS Polymer Preprints, vol. 18, No. 2, pp. 1-4 (Aug. 1977).
Blumstein, A. et al., ACS Polymer Preprints, vol. 18, No. 2, pp. 14-20 (Aug. 1977).
Kelker, H. et al., Mol. Cryst. Liq. Cryst (Lett), vol. 49, pp. 175-177 (Mar. 1979).
Finkelmann, H. et al., Makromol. Chem., vol. 179, pp. 829-832 (Mar. 1978), pp. 273-276 (Jan. 1978).
Klanderman, B. et al., JACS, vol. 97, No. 6, pp. 1585-1586 (1975).
Amerik, Y. et al., Abst. 6th Int. Liq. Cryst. Conf., G-4 (Aug. 1976).
Dubois, J. C. et al., ACS Polymer Preprints, vol. 18, No. 2, pp. 63-66 (1977).
Hsu, E. et al., Mol. Cryst. Liq. Cryst., vol. 33, pp. 35-45 (1976).
Gray, C. et al., Mol. Cryst. Liq. Cryst., vol. 37, pp. 189-211 (1976), pp. 157-188 (1977).
Gray, C. et al., Mol. Cryst. Liq. Cryst. (Lett), vol. 34, pp. 211-217 (1977).
Finkeman, H. et al., Z Naturforsch., vol. 28a, pp. 799-800 (1973).
Baessler, H. et al., J. Chem. Physics, vol. 52, pp. 631-637 (1970).

*Primary Examiner*—Teddy S. Gron
*Attorney, Agent, or Firm*—Keil & Witherspoon

[57] ABSTRACT

A liquid-crystalline polymer phase having an induced cholesteric structure comprises a component having a chiral structure and a component having a nematic structure and contains a polymer with nematogenic units of the formula

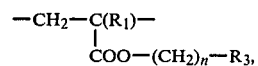

wherein $R_1$ is hydrogen or methyl, n is an integer from 1 to 6 and $R_3$ represents specific structural elements containing at least two phenylene groups. Preferred is a copolymer comprising a component of the above formula and an additional chiral component of similar structure, prepared by copolymerization of the nematogenic monomer with the chiral monomer.

The liquid-crystalline polymer phase permits variation of the wavelength of the reflected light $\lambda_R$, and its cholesteric structure can be converted to the glassy polymer state and remains preserved in the solid state. Such liquid-crystalline polymer phases can be used in integrated optics, opto-electronics and information storage, e.g. for the manufacture of polarization filters or selective reflectors.

9 Claims, No Drawings

LIQUID-CRYSTALLINE POLYMER PHASE HAVING A CHOLESTERIC STRUCTURE, PROCESSES FOR ITS PREPARATION AND ITS USE

The present invention relates to a liquid-crystalline polymer phase having a cholesteric structure, which comprises chiral and nematic components, and to processes for its preparation, and its use.

Low molecular weight liquid crystals having a nematic, smectic or cholesteric structure have been disclosed, and because of their optical properties have found uses, inter alia, in opto-electronics and non-destructive material testing. Because of their high optical rotation and the circular dichroism, which results from selective reflection of circular-polarized light of wavelength $\lambda_R$, the low molecular weight cholesteric liquid crystals are of particular industrial importance. Their helical superstructure, characterized by the pitch p, is directly related to the wavelength of the reflected light $\lambda_R$.

It has also been disclosed that by admixture of chiral compounds, cholesteric helix structures can be induced in low molecular weight nematic liquid crystals (Z. Naturforschung, 28A (1973), 799), the pitch p and the wavelength $\lambda_R$ depending on the structure and concentration of the chiral component and being, accordingly, capable of variation. It is a disadvantage that this optical behavior of the low molecular weight cholesteric compounds or of the low molecular weight mixtures showing induced cholesteric structure is only observed in the liquid-crystalline phase and hence in a specific temperature range, without the possibility of achieving the cholesteric structure in a solid phase.

It is true that a copolymer has been disclosed which retains its cholesteric structure even in the solid phase (Makromol. Chem. 179 (1978), 829–832). However, the cholesteric structure is only observed at a monomer ratio of about 1:1; variation of the pitch p and of the wavelength $\lambda_R$ is not possible.

It is an object of the present invention to provide a liquid-crystalline polymer phase having a cholesteric structure, which phase does not suffer from the disadvantages indicated and instead permits variation of the wavelength of the reflected light $\lambda_R$, and the cholesteric structure of which can, without substantial variation, be converted to the glassy polymer state and remains preserved in the solid state.

We have found that this object is achieved, surprisingly, by a liquid-crystalline polymer phase having a cholesteric structure, which comprises one or more components which without addition of another component have a nematic structure, and one or more further components having a chiral structure.

The polymer phase contains a homopolymer or copolymer with nematogenic units of the following formula:

$$\left[ \begin{array}{c} -CH_2-C(R_1)- \\ | \\ COO-(CH_2)_n-R_3 \end{array} \right]$$

where $R_1$ is hydrogen or methyl, n is an integer from 1 to 6 and $R_3$ is

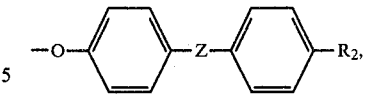

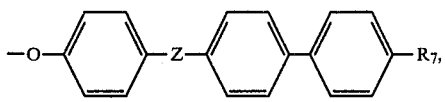

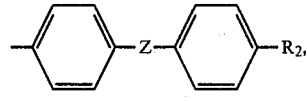

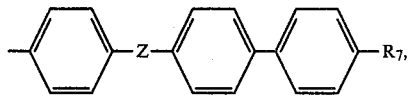

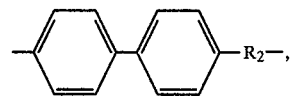

where Z is —COO— or —OCO—, $R_2$ is —O(CH$_2$)$_m$H, —(CH$_2$)$_m$H or —COO—(CH$_2$)$_m$H, m being an integer from 1 to 6, and $R_7$ is hydrogen or $R_2$.

The invention also provides the processes described in the claims, and the use of the new product.

Nematic homopolymers comprising these units are in part disclosed in Makromol. Chem. 179 (1978), 273–276. In particular, they exhibit a nematic structure if n or m is small and hence at least one of the carbon chains is short. In the polymer phase according to the invention, having an induced cholesteric structure, the polymer is mixed with one or more low molecular weight (molecular weight less than 3000) or polymeric chiral substances; preferably, the compound is a copolymer comprising at least one component of the above formula and at least one additional polymerizable component which is chiral. The low molecular weight chiral component need not necessarily be mesomorphous, but is, particularly advantageously, a cholesteric compound, eg. act-octyl p-methoxybenzylidene-p'-aminocinnamate or p-cyanobenzylidene-1-(-)-α-methylbenzylamine. It is preferred that the molecular structure of these low molecular weight chiral components should be similar to that of the monomer of the nematic polymer, in order to achieve good miscibility of the two components. Furthermore, because of the liquid-crystalline structure of these low molecular weight chiral components, and the attendant relatively high helical twisting power, systems with reflection wavelengths extending into the visible range can be obtained.

Suitable chiral components for inducing the cholesteric structure are monomers of the formula $CH_2$=$CR_1$—COO—$(CH_2)_n$—$R_4$ ($R_1$, $R_4$ and n having the meanings given below) and polymers thereof. Preferably, the chiral component comprises a homopolymer, or especially a copolymer with nematic comonomers, containing units of the following formula, which is very similar to the formula of the nematic component:

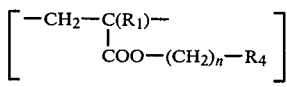

in which $R_1$ is hydrogen or methyl, n is an integer from 1 to 10 and $R_4$ is

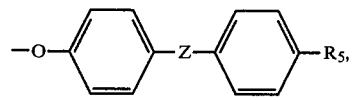

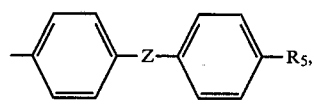

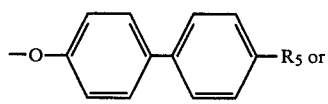

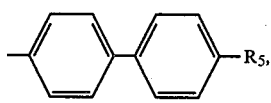

where Z is COO— or OCO— and $R_5$ is —CH=N—$R_6$, —$OR_6$, —$COOR_6$, —CH=CH—$COOR_6$ or —$R_6$, $R_6$ being alkyl or alkylaryl of 4 to 10 carbon atoms, and having at least one asymmetric carbon atom.

Preferably, $R_6$ is branched alkyl, for example amyl or octyl, or has, for example, one of the following structures:

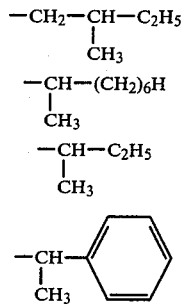

The chiral component, as monomer or polymer such as a homopolymer, can also exhibit a liquid-crystalline structure, but this is not absolutely essential for achieving the object of the invention.

The chiral component can be a homopolymer mixed with the nematic homopolymer. However, it is very particularly advantageous if the polymer phase according to the invention is a copolymer which has been prepared from monomers of the formulae

and

The first formula is that of the nematic component and the second formula that of the chiral component, and $R_1$, $R_3$, $R_4$ and n have the above meanings.

The copolymerization of the nematogenic monomer with the chiral monomer, using a monomer mixture of concentration $x_1$, only gives a copolymer in which the proportion of copolymerized units corresponds to the monomer concentration $x_1$ if the copolymerization parameters of the monomeric components are of comparable order of magnitude. This is of particular importance if a cholesteric copolymer of a certain composition is to be prepared without trouble, for example without taking the reaction kinetics into account. Hence, it is preferred to employ monomer components which have comparable copolymerization parameters, namely alkyl acrylates or alkyl methacrylates which primarily differ in respect of the substituents $R_3$ and $R_4$ in the $\omega$-position of the alkyl chain.

In copolymers of nematogenic components with chiral components which however are not themselves mesomorphous, the chiral component can only be added to the nematic phase up to a certain limiting concentration, since otherwise the phase which exhibits induced cholesteric properties is destroyed. The limiting concentration is essentially determined by the molecular structure of the chiral component. In order to achieve high concentrations of the latter (greater than about 10 mole %), it is advantageous if the molecular structure of the chiral component substantially corresponds to that of the nematic component.

For this reason, the preferred copolymer in particular comprises nematic and chiral components of the above formulae in which $R_3$ and $R_4$ are also preferably substantially similar in structure and especially only differ in respect of the $R_2$ group and the (—CH=N—$R_6$), (—$OR_6$), (—$COOR_6$), (—CH=CH—$COOR_6$) or (—$R_6$) group.

The preferred chiral monomers for the preparation of the induced cholesteric copolymer accordingly essentially only differ from the nematogenic monomers in respect of the chiral structural element; the remaining structural elements, for example the polymerizable group, are preferably identical, since this results in comparable copolymerization parameters. The choice of the chiral structural element determines the helical twisting power and hence the magnitude of the reflected wavelength as a function of the concentration of the chiral component.

A measure of the ability of low molecular weight molecules to induce helical superstructures, ie. cholesteric structures, in low molecular weight compounds having a nematic structure, is referred to as the helical twisting power (J. chem. Physics 52 (1970), 631).

Surprisingly, it is found that analogously to the low molecular weight chiral-nematic mixed systems, the reciprocal reflection wavelength $1/\lambda_R$ of the polymer phase according to the invention increases with increasing proportion of chiral component. For different chiral components present in the same proportion, different values of $1/\lambda_R$ of the polymer phase according to the invention are found, which evidently depends on the particular structure of the chiral component, and this phenomenon is attributed to the helical twisting power of the chiral component. Accordingly, using the novel polymer phases, it is possible to vary $\lambda_R$ over a wide range by varying the nature and concentration of the chiral component.

An induced cholesteric copolymer which reflects in the visible wavelength range should accordingly contain a chiral component having a high helical twisting power. The chiral structural element in this copolymer is preferably a [—CH=N—CH(CH₃)C₆H₅] group. If, on the other hand, reflection in the infra-red range is required, the helical twisting power of the chiral component can be relatively low. Preferably the chiral structural element is, in this case, an alkoxy group having at least one asymmetric C atom, for example a 2-methylbutoxy group. A low helical twisting power is exhibited by chiral monomers of the structure

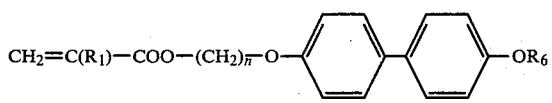

A copolymer with induced cholesteric properties, which contains this component, reflects in the infra-red wavelength range.

It has been found, surprisingly, that a homogeneous texture which reflects circular-polarized light (Grandjean texture) arises spontaneously with the polymer phase of the invention, without employing external factors, eg. electrical or magnetic fields, above the glass transition temperature $T_G$.

The longest-wavelength absorption maximum of the compounds with induced cholesteric character may be less than 350 nm, so that absorption in the visible wavelength range does not occur. Provided the wavelength of the reflected light $\lambda_R$ lies outside the visible wavelength range, the compound according to the invention is completely transparent, colorless and clear, in the isotropic phase (ie. above the clearing temperature $T_{Cl}$), in the liquid-crystalline phase and in the glassy state, provided that uniform orientation of the phase has taken place at temperatures below the clearing temperature.

The particular advantage of the novel polymer phase exhibiting induced cholesteric character is the further possibility that the cholesteric texture which selectively reflects circular-polarized light (Grandjean texture) can be fixed by lowering the temperature to below the glass transition temperature $T_G$, ie. can be fixed in the solid state. Because of these properties, the polymer phase according to the invention, in addition to being useful in virtually all technical fields in which low molecular weight cholesteric systems are used, is capable of having an orientation, and hence the information corresponding thereto, introduced into the glassy state, and stored therein, merely by lowering the temperature to below the glass transition temperature.

For example, for use as a store element, the polymer phase is processed as a viscous liquid above the glass transition temperature and the position of the optical axis is fixed by elecrical or magnetic fields. The form and structure of the orientation, which can be in the nature of information, is then fixed by cooling to below the glass transition temperature $T_G$.

Finally, there are numerous other possible applications in the field of integrated optics, opto-electronics and information storage because of the fact that the polymer phase according to the invention combines cholesteric properties with typical polymer properties, for example the ability to form coatings, films and fibers, easy moldability and the like. These properties can be modified in the conventional manner by copolymerization, mixing with other components, variation of molecular weights, addition of a large variety of inorganic or organic additives and metals, and a large number of other treatments familiar to those skilled in the art.

For example, the polymer phase described may be used to prepare circular polarization filters or selective reflectors. If two filters or reflectors, which reflect the same wavelength $\lambda_R$ but exhibit opposite helical structures of the cholesteric phase, are used in series, selective reflectors are obtained. The opposite helical structure results, for example, from using the optical antipodes of the chiral component. The reflection wavelength of the selective reflectors can also be adjusted to a value suitable for infrared radiation, the material transmitting the other wavelength ranges except the wavelength ranges of its intrinsic absorption. If, on the other hand, the polymer phase is applied to a light-transmitting support having $\lambda_R/4$ properties, selective linear polarization filters and reflectors can be prepared. Filters of this nature are employed in display technology (Scheffer cell).

The monomers

and

can be prepared from conventional compounds by conventional methods. Examples of possible methods of preparation are shown below. The radicals $R_1$, $R_2$, $R_3$, $R_4$ and $R_5$, and the parameters m and n, have the above meanings, ie. the monomers containing the radical $R_3$ are nematic compounds and the monomers containing the radical $R_4$ are chiral compounds.

To prepare the monomers of the general formula

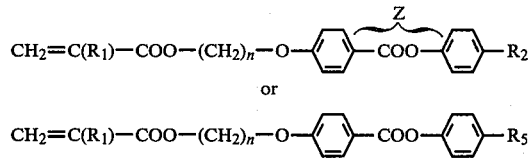

the compounds known per se, of the formula

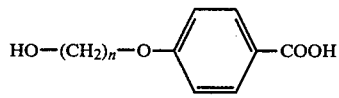

are used as starting materials. The polymerizable acrylyl or methacrylyl group is preferably introduced by azeotropic esterification using conventional methods, and monomers of the formula

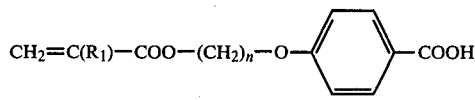

are obtained, eg. 4-(ω-propenoyloxy-ethoxy)-benzoic acid, 4-(ω-propenoyloxy-propoxy)-benzoic acid, 4-(ω-propenoyloxybutoxy)-benzoic acid, 4-(ω-propenoyloxy-pentoxy)-benzoic acid, 4-(ω- propenoyloxy-hexoxy)-benzoic acid, 4-[ω-(2-methyl-propenoyloxy)-ethoxy]-benzoic acid, 4-[ω-(2-methyl-propenoyloxy)-propoxy]-benzoic acid, 4-[ω-(2-methyl-propenoyloxy)-butoxy]-benzoic acid, 4-[ω-(2-methyl-propenoyloxy)pentoxy]-benzoic acid and 4-[ω-(2-methylpropenoyloxy)hexoxy]-benzoic acid.

The p-substituted, polymerizable benzoic acids are esterified by conventional methods with the phenolic derivatives of the formula

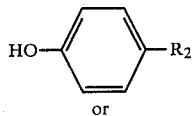
or
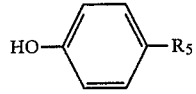

which are known per se. The phenolic derivatives employed in the last stage are hydroquinone monoalkyl ethers, p-alkylphenols, alkyl p-hydroxybenzoates, 4-hydroxy-4'-alkoxydiphenylenes, 4-hydroxy-4'-alkyldiphenylenes, alkyl p-hydroxycinnamates or azomethines, which are known per se. The monomers mentioned above (where Z is COO) are obtained.

To prepare the monomers of the general formula

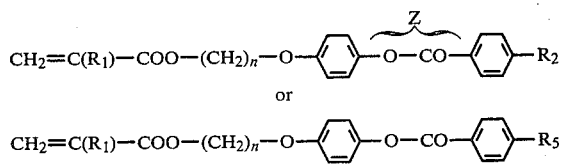

compounds known per se, of the formula

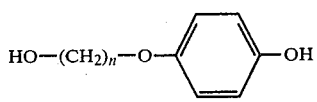

are used as starting materials. The polymerizable acrylyl or methacrylyl group is preferably introduced by azeotropic esterification using conventional methods, and monomers of the general formula

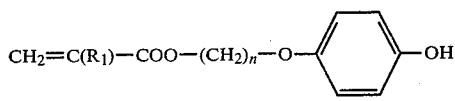

are obtained, eg. 4-(ω-propenoyloxy-ethoxy)-phenol, 4-(ω-propenoyloxy-propoxy)-phenol, 4-(ω-propenoyloxy-butoxy)-phenol, 4-(ω-propenoyloxy-pentoxy)-phenol, 4-(ω-propenoyloxyhexoxy)-phenol, 4-[ω-(2-methylpropenoyloxy)-ethoxy]-phenol, 4-[ω-(2-methylpropenoyloxy)-propoxy]-phenol, 4-[ω-(2-methylpropenoyloxy)-butoxy]-phenol, 4-[ω-(2-methylpropenoyloxy)pentoxy]-phenol and 4-[ω-(2-methylpropenoyloxy)-hexoxy]phenol.

These polymerizable compounds are esterified, using conventional methods, with p-substituted benzoic acids known per se, of the general formula

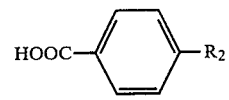
or
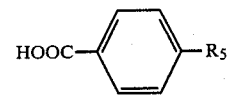

Preferably, these compounds are p-alkoxybenzoic acids or p-alkylbenzoic acids. The above monomers (where Z is OCO) are obtained.

To prepare the monomers of the general formula

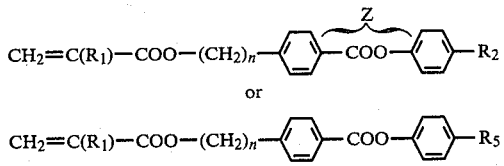

compounds known per se, of the formula

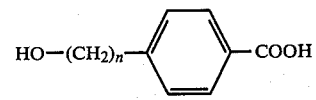

are used as starting materials. The polymerizable acrylyl or methacrylyl group is preferably introduced by azeotropic esterification, using conventional methods, and monomers of the formula

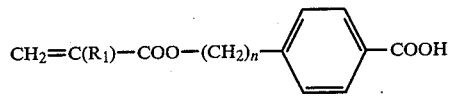

are obtained. The p-substituted, polymerizable benzoic acids are esterified by conventional methods with phenolic derivatives known per se, of the formula

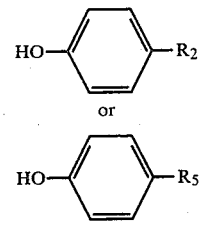
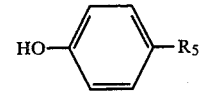

The above monomers (where Z is COO) are obtained.

To prepare the monomers of the general formula

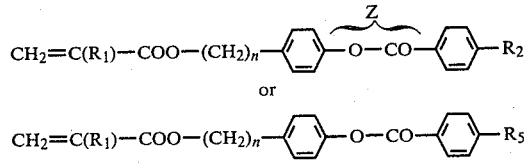

compounds known per se, of the formula

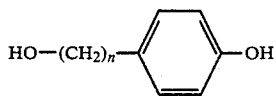

are used as starting materials. The polymerizable acrylyl or methacrylyl group is preferably introduced by azeotropic esterification, using conventional methods, and the monomers of the following formula

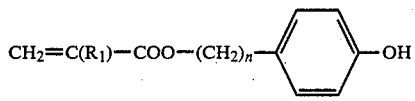

are obtained. The polymerizable compounds are esterified by conventional methods with p-substituted benzoic acids known per se, of the general structure

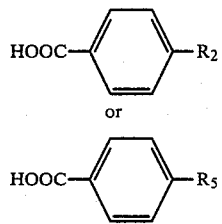

The above monomers (where Z is OCO) are obtained.

To prepare the monomers of the general formula

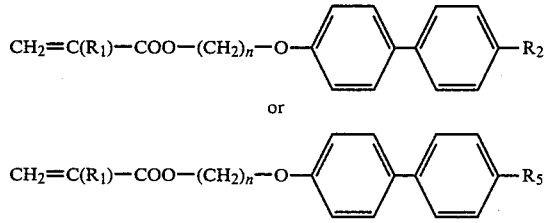

compounds known per se, of the formula

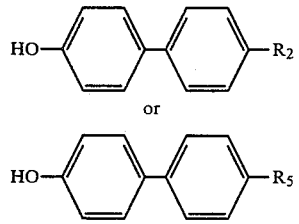

are used as starting materials and are reacted with ω-hydroxyalkyl halides known per se, eg.

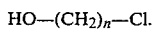

Where n is 4 or 5, it is preferred to carry out the reaction with an ω-halocarboxylic acid, eg.

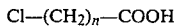

instead of with an ω-hydroxyalkyl halide, the carboxyl group subsequently being reduced to the hydroxyl group.

In the resulting compounds of the formula

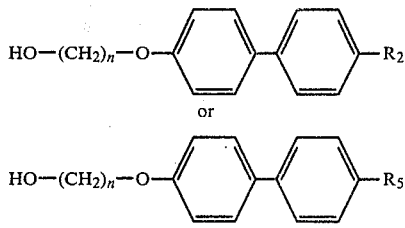

the polymerizable acrylyl or methacrylyl group is preferably introduced by azeotropic esterification using conventional methods. The above monomers are obtained, in particular the following chiral monomers: 4-(ω-propenoyloxy)-ethoxy4'-(2-methylbutoxy)-biphenyl, 4-(ω-propenoyloxy)-propoxy4'-(2-methylbutoxy)-biphenyl, 4-(ω-propenoyloxy)-hexoxy-4'-(2-methylbutoxy)-biphenyl, 4-(ω-propenoyloxy)-ethoxy-4'-(1-methylheptoxy)-biphenyl, 4-(ω-propenoyloxy)-propoxy-4'-(1-methylheptoxy)-biphenyl, 4-(ω-propenoyloxy)-hexoxy-4'-(1-methylheptoxy)-biphenyl, 4-(ω-propenoyloxy)-ethoxy-4'-(1-methylpropoxy)-biphenyl, 4-(ω-propenoyloxy)-propoxy-4'-(1-methylpropoxy)-biphenyl, 4-(ω-propenoyloxy)-hexoxy-4'-(1-methylpropoxy)-biphenyl, 4-[ω-(2-methylpropenoyloxy)]-ethoxy-4'-(2-methylbutoxy)-biphenyl, 4-[ω-(2-methylpropenoyloxy)]-propoxy-4'-(2-methylbutoxy)-biphenyl, 4-[ω-(2-methylpropenoyloxy)]-hexoxy-4'-(2-methylbutoxy)-biphenyl, 4-[ω-(2-methylpropenoyloxy)]-ethoxy-4'-(1-methylheptoxy)-biphenyl 4-[ω-(2-methylpropenoyloxy)]-propoxy-4'-(1-methylheptoxy)-biphenyl, 4-[ω-(2-methylpropenoyloxy)]-hexoxy-4'-(1-methylheptoxy)-biphenyl, 4-[ω-(2-methylpropenoyloxy)]-ethoxy-4'-(1-methylpropoxy)-biphenyl, 4-[ω-(2-methylpropenoyloxy)]-propoxy-4'-(1-methylpropoxy)-biphenyl and 4-[ω-(2-methylpropenoyloxy)]-hexoxy-4'-(1-methylpropoxy)-biphenyl.

The homopolymers or copolymers of the monomers

and

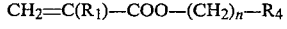

are preferably prepared by free radical polymerization. The reaction is started, for example, by UV radiation or by using free radical initiators. The polymerization can be carried out in solution or as a mass polymerization, without a detectable polymer-monomer phase separation occurring.

The polymer and monomer are miscible in any desired proportions, and hence the properties of the resulting product can be varied. The chiral monomer itself can be mesomorphous, ie. liquid-crystalline, but this characteristic is not absolutely essential. However, if the chiral comonomer is not itself mesomorphous, a certain limiting concentration must not be exceeded, since otherwise the mesomorphous phase is destroyed. The limiting concentration up to which the cholesteric phase remains preserved depends on the structure of the chiral component.

To prepare mixtures, the nematogenic homopolymer prepared from the monomer, and the chiral homopolymer are conjointly dissolved in, for example, an organic solvent, and the solution is freeze-dried. The mixture of the two homopolymers, freed from the solvent, exhibits an induced cholesteric structure in the liquid-crystalline phase. A mixture of a nematic homopolymer with a low molecular weight chiral compound is prepared in the same way, but the structure of the low molecular weight component must be selected to be such that the two components are miscible.

The Examples which follow illustrate the invention. Examples 1 and 2 describe the preferred nematogenic monomers, and Examples 3 and 4 the preferred chiral monomers. Example 5 describes a copolymer having induced cholesteric characteristics and Example 6 a mixture having induced cholesteric characteristics.

EXAMPLE 1

The text which follows describes the preparation of various monomers of the general formula

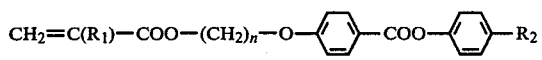

where $R_1$ is hydrogen or methyl, n is 2, 3 or 6, and $R_2$ is $-O-(CH_2)_mH$ (where m is 1 or 2), $-CH_3$,

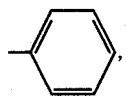

or

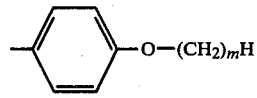

(where m is 1 or 2).

1.1. Starting from compounds known per se, of the structure

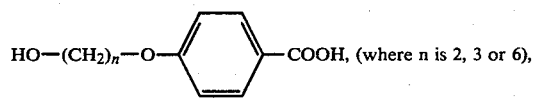

the polymerizable acrylyl or methacrylyl group is introduced by azeotropic esterification using conventional methods:

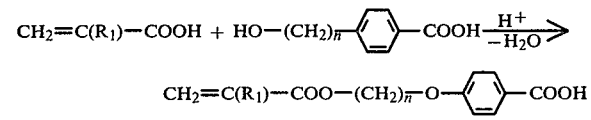

1.1.1. Preparation of 4-(2-propenoyloxy)-ethoxy-benzoic acid 50 g of p-(2-hydroxyethoxy)-benzoic acid, 120 g of acrylic acid, 5 g of p-toluenesulfonic acid and 5 g of hydroquinone as an inhibitor, in 200 ml of chloroform, are refluxed for 5 hours in a 500 ml flask fitted with a water separator and reflux condenser. The cooled reaction solution is then poured into about 1 liter of ether and is washed with 5 portions of water each of about 200 ml. After drying the ether phase with Na$_2$SO$_4$, the solvents are stripped off, the product is dissolved in a small amount of ethanol and petroleum ether is added until the solution only just remains clear. On cooling to $-15°$ C., the product precipitates. Recrystallization is repeated until the substance appears pure in a thin layer chromatogram (silica gel, with a 4:1 ethyl acetate/hexane mixture as the mobile phase).

4-(3-Propenoyloxy)-propoxy-benzoic acid and 4-(6-propenoyloxy)-hexoxy-benzoic acid are prepared by similar methods.

1.1.2. Preparation of 4-[2-(2-methylpropenoyloxy)-ethoxy]-benzoic acid 50 g of p-(2-hydroxyethoxy)-benzoic acid, 130 g of methacrylic acid, 5 g of p-toluenesulfonic acid and 5 g of hydroquinone as an inhibitor are dissolved in 200 ml of CHCl$_3$ and the solution is refluxed in a 500 ml flask, fitted with a water separator and reflux condenser, until about 6 ml of water have separated out (about 20 hours). The cooled solution is introduced into about 1 liter of ether and is washed with 5 portions of water each of about 200 ml. After drying the solution with Na$_2$SO$_4$, the solvents are stripped off and the crude product is recrystallized as described under 1.1.1.

4-[3-(2-Methylpropenoyloxy)-propoxy]-benzoic acid and 4-[6-(2-methylpropenoyloxy)-hexoxy]-benzoic acid were prepared in a similar manner.

1.2.1. The p-substituted, polymerizable benzoic acids prepared under 1.1.1. and 1.1.2. are esterified by conventional methods with hydroquinone monoalkyl ethers known per se, of the general structure

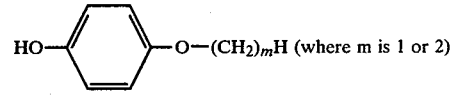

to give compounds of the structure

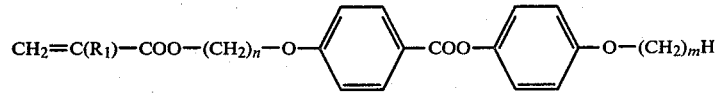

(where n is 2, 3 or 6), compounds where m+n is greater than 8 leading to smectic polymers.

Embodiment A, illustrated by the example of 4-[2-(2-methylpropenoyloxy)-ethoxy]-benzoic acid (4'-methoxy)-phenyl ester (n=2; m=1).

4.6 g of sodium are dissolved in 50 ml of absolute ethanol in a 100 ml flask and 24.0 g of hydroquinone monomethyl ether are then added. The solution is cooled to $-15°$ C. and the acid chloride prepared from 22.7 g of 4-[2-(2-methylpropenoyloxy)-ethoxy]-benzoic acid and 40 ml of thionyl chloride is slowly added dropwise, whilst stirring. The solution is then stirred for about 4 hours at $-15°$ C., and thereafter overnight at room temperature. The batch is then taken up in 500 ml of ether and washed once with aqueous NaHCO₃ solution and with 3 portions of water each of 100 ml. After drying with Na₂SO₄, the solvents are stripped off.

Embodiment B, illustrated by the example of 4-(2-propenoyloxy)-ethoxy-benzoic acid (4'-methoxy)-phenyl ester 11.8 g of 4-(2-propenoyloxy)-ethoxy-benzoic acid, 6.2 g of hydroquinone monomethyl ether and a few mg of 1,3-dinitrobenzene as an inhibitor are dissolved in 50 ml of absolute tetrahydrofuran (anhydrous) and 25 ml of CH₂Cl₂ in a 250 ml flask equipped with a dropping funnel and drying tube (CaCl₂), and the solution is cooled with ice. 11.3 g of dicyclohexylcarbodiimide, dissolved in 20 ml of CH₂Cl₂, are slowly added dropwise to the preceding solution, whilst stirring. The mixture is then left to stand, whilst being stirred, for about 3 hours at 0° C. and thereafter overnight at room temperature. The dicyclohexylurea which has precipitated is then filtered off and the solution is concentrated. The residue is taken up in acetonitrile and urea which has precipitated is again filtered off. Thereafter, the acetonitrile is stripped off.

Working-up method for Embodiment A and Embodiment B

The crude products are taken up in ethyl acetate (to give about 20% strength solutions) and are cooled to −15° C. to cause them to crystallize. The products which have precipitated are filtered off with suction; in the case of low-melting compounds, particularly the acrylic compounds, a cooled suction filter is used. The recrystallization is repeated as often as is necessary to give a compound in which impurities cannot be detected by thin layer chromatography (silica gel, using a 1:4 mixture of hexane/ethyl acetate as the mobile phase).

The following monomer, which can form a nematic polymer, is prepared by a similar method, using compounds where n is 6 and m is 1.

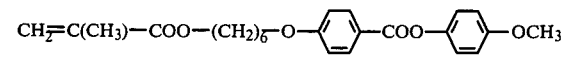

1.2.2. The p-substituted, polymerizable 4-[6-(2-methylpropenoyloxy)-hexoxy]-benzoic acid prepared under 1.1.2. is esterified by conventional methods with 4-methylphenol, a compound known per se, to give the compound of the structure

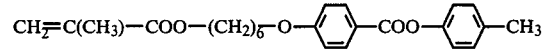

Esterification and working up take place by the method described under Section 1.2.1.

1.2.3. The p-substituted, polymerizable 4-[2-(2-methylpropenoyloxy)-ethoxy]-benzoic acid prepared as described under 1.1.2. is esterified by conventional methods with 4-hydroxy-4'-ethoxy-biphenyl, a compound known per se, of the structure

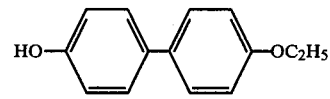

to give the compound of the structure

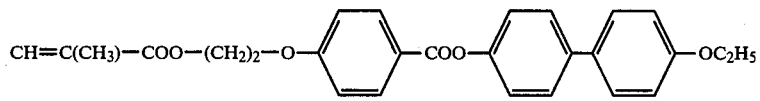

The esterification may be carried out according to Embodiment A or Embodiment B, described under 1.2.1. The product is worked up as described under 1.2.1.

Using a similar method with 4-hydroxy-4'-methoxybiphenyl gives

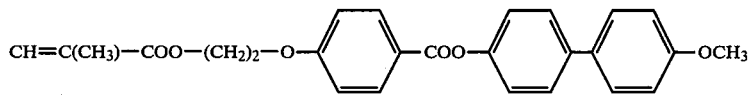

A similar esterification of 4-[6-(2-methylpropenoyloxy)-hexoxy]-benzoic acid, prepared under 1.1.2., with 4-hydroxy-4'-methoxy-biphenyl gives the following monomer

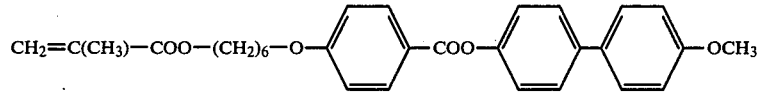

1.2.4. The p-substituted, polymerizable benzoic acids prepared under 1.1.1. and 1.1.2., namely 4-[3-(2-methylpropenoyloxy)-propoxy]-benzoic acid, 4-[6-(2-methylpropenoyloxy)-hexoxy]-benzoic acid and 4-(6-propenoyloxy-hexoxy)benzoic acid are esterified by conventional methods with p-hydroxy-biphenyl

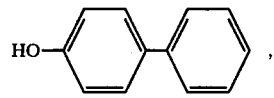

a compound known per se, to give compounds of the structure

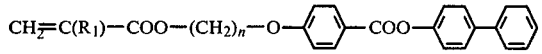

where $R_1$ is H and n is 6, or $R_1$ is $CH_3$ and n is 3 or 6.

The esterification may be carried out according to Embodiment A or Embodiment B described under 1.2.1. The products are worked up as described in 1.2.1.

In the case of the last-mentioned monomers where $R_1$ is H and n is 6, or $R_1$ is $CH_3$ and n is 6, the methyl group in the polymerizable methacrylyl group in the latter compound is replaced by hydrogen in the former compound, the structure of the mesogenic groups being otherwise the same. The polymer phases prepared from the two monomers exhibit the same liquid-crystalline characteristics, with the phase transitions shifted. This behavior was generally found with similar compounds according to the invention.

EXAMPLE 2

2.1. The text which follows describes the preparation of some monomers according to the invention, of the formula

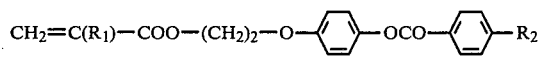

where $R_1$ is hydrogen or methyl and $R_2$ has the above meaning. Starting from compounds known per se, of the formula

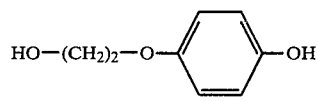

the polymerizable acrylyl or methacrylyl group is introduced by azeotropic esterification, using conventional methods.

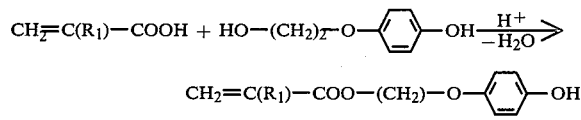

2.1.1. Preparation of 4-(2-propenoyloxy-ethoxy)-phenol 50 g of p-(hydroxyethoxy)-phenol, 110 g of acrylic acid, 5 g of p-toluenesulfonic acid and 5 g of hydroquinone as an inhibitor, in 200 ml of chloroform, are refluxed for 5 hours in a 500 ml flask fitted with a water separator and reflux condenser. The cooled reaction solution is then introduced into about 1 liter of ether and is washed with 5 portions of water each of about 200 ml.

After drying the ether phase with $Na_2SO_4$, the solvents are stripped off, the product is dissolved in ethanol, and petroleum ether is added until the solution just remains clear. On cooling to $-15°$ C., the product precipitates. The recrystallization is repeated until the substance appears pure in a thin layer chromatogram (silica gel, using a 4:1 ethyl acetate/hexane mixture as the mobile phase).

2.1.2. Preparation of 4-[2-(2-methylpropenoyloxy)-ethoxy]-phenol.

50 g of p-(hydroxyethoxy)-phenol, 120 g of methacrylic acid, 5 g of p-toluenesulfonic acid and 5 g of hydroquinone as an inhibitor are dissolved in 200 ml of $CHCl_3$ and refluxed in a 500 ml flask, equipped with a water separator and reflux condenser, until about 5 ml of water have separated out (about 20 hours). The cooled solution is introduced into about 1 liter of ether and washed with 5 portions of water each of about 200 ml. The solution is then dried with $Na_2SO_4$, the solvents are stripped off and the crude product is recrystallized as described under 1.1.1. 2.1.3. The p-substituted polymerizable phenols prepared under 2.1.1. and 2.1.2. are esterified by conventional methods with p-substituted benzoic acids known per se, of the general structure

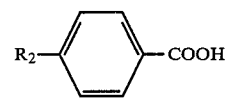

to give compounds of the structure

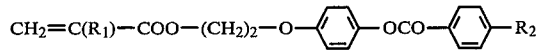

2.2. The monomers according to the invention, of the formula

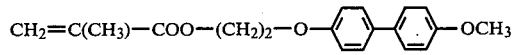

are prepared under the reaction conditions described in EXAMPLE 4 below, in accordance with the equation

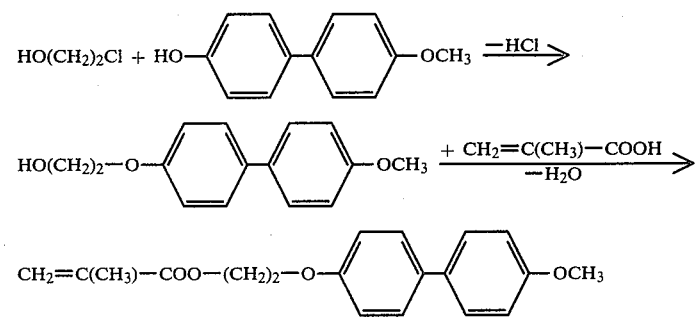

EXAMPLE 3

The text which follows describes the preparation of the chiral monomers (d- or l-antipode) of the formula

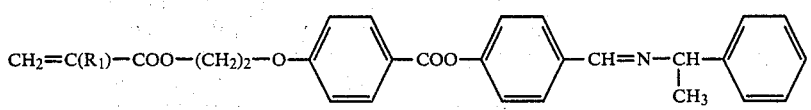

where R₁ is H or CH₃, and

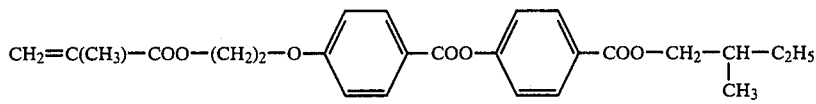

These monomers consist of a polymerizable group, a structural element of similar structure to the nematogenic copolymerization component, and the preferred chiral structural element.

The benzoic acids

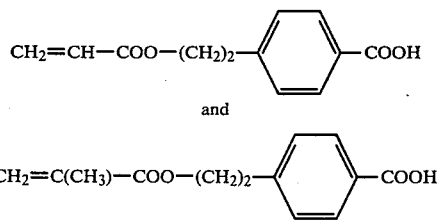

described under 1.1.1. and 1.1.2. above are used as starting materials and are converted by esterification with the chiral phenols (d- or l-antipode)

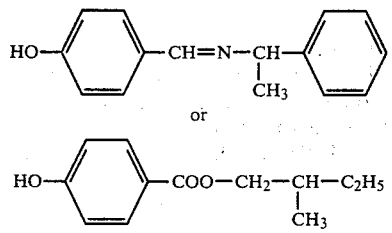

using conventional methods, to the above monomers, for example as follows:

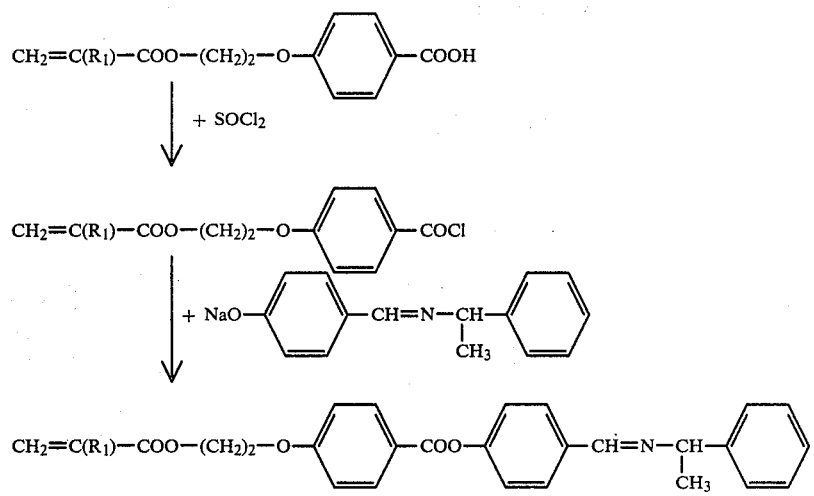

3.1.1. Preparation of 4-hydroxybenzylidene-1-phenylethylimine 16 ml of d-1-phenylethylamine (or of the 1-component) are added dropwise to a hot solution of 15 g of p-hydroxybenzaldehyde in 150 ml of toluene, whereupon the reaction to give the Schiff base occurs immediately. Water formed is distilled off azeotropically (using a water separator). When the equimolar amount of water has been separated off, the solution is allowed to cool and the reaction product is filtered off and recrystallized from ethanol (melting point 170° C., with decomposition).

3.1.2. Preparation of 4-(2-propenoyloxyethoxy)-benzylidene1-phenylethylimine a. Preparation of the phenolate solution:

42 millimoles of sodium are added to 40 ml of absolute ethanol, whilst excluding moisture. After the sodium has reacted completely, 42 millimoles of the Schiff base prepared according to 3.1.1. are added.

b. 25 ml of thionyl chloride and two drops of dimethylformamide are added to 42 millimoles of 4-(ω-propenoyloxyethoxy)-benzoic acid at room temperature and the mixture is left to stand for about 5 hours (during which HCl and SO₂ are evolved). Excess thionyl chloride is then completely removed under reduced pressure. The acid chloride which remains is taken up in 20 ml of absolute ether and is slowly added dropwise to the phenolate solution at room temperature, whilst stirring. When all the acid chloride has been added, the mixture is stirred for 2 hours. 250 ml of ether are then added to the batch and the ether solution is washed 3 times with water and dried with Na₂SO₄, after which the solvent is stripped off.

The crude product is recrystallized from ethanol.

4-[2-(2-Methylpropenoyloxy)-ethoxy]-benzylidene-1-phenylethylimine (d- or l-antipode) is prepared by a similar method from 4-[2-(2-methylpropenoyloxy)-ethoxy]-benzoic acid and the above chiral phenol (d- or l-antipode).

3.2. The compound

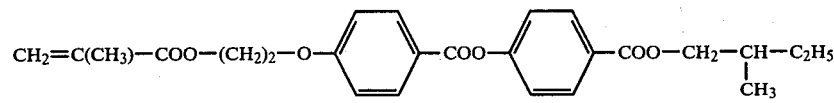

is prepared by the method of esterification and working up described in Section 1.2.1.

EXAMPLE 4

The text which follows describes the preparation of the chiral monomer (d- or l-antipode) of the formula

(where $R_1$ is H or $CH_3$). This monomer comprises a polymerizable group, an element of similar structure to that of the nematogenic copolymerization component, and the preferred chiral structural element.

The synthesis is carried out in accordance with the following equations:

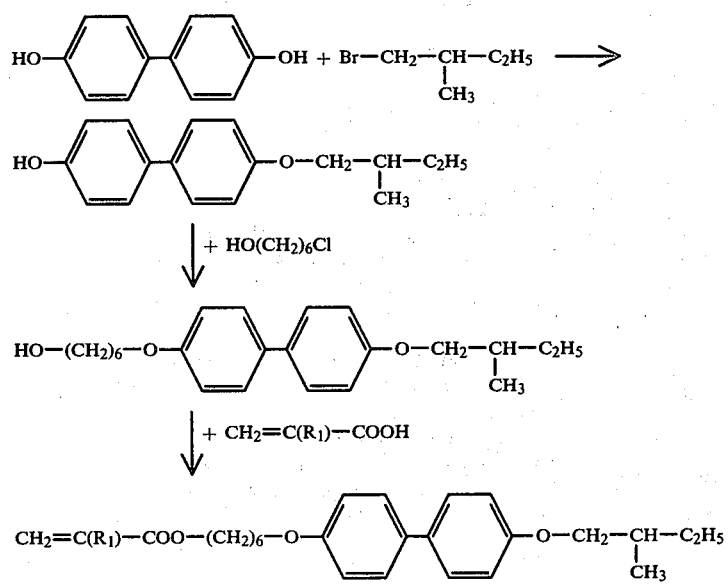

4.1. Preparation of 4-(2-methylbutoxy)-4'-hydroxybiphenyl 0.5 mole (11.5 g) of sodium is added cautiously to 300 ml of absolute ethanol, whilst excluding moisture. When the sodium has dissolved, 0.5 mole (93 g) of 4,4'-dihydroxybiphenyl is added. The reaction batch is raised to reflux and 0.5 mole (75.5 g) of optically active 1-bromo-2-methylbutane is slowly added dropwise, with vigorous stirring. After completion of the addition, refluxing is continued for about 5 hours. When the reaction solution has cooled, the NaBr which has precipitated is removed by decanting, the ethanol is stripped off, the crude product is introduced into 10% strength aqueous sodium hydroxide solution and this mixture is raised to the boil. The diether formed as a by-product is insoluble at the boil and is removed by filtration. On cooling the filtrate, the sodium salt of the monoether precipitates. It is filtered off and recrystallized once more from 10% strength NaOH. The Na salt is then dissolved in water and the phenol is precipitated by acidifying the solution with HCl. The phenol is filtered off, washed with water and dried (melting point 135° C.).

4.2. Preparation of 4-(6-hydroxyhexoxy)-4'-(2-methylbutoxy)-biphenyl 4.5 g of KOH and 15 g of 4-hydroxy-4'-(2-methylbutoxy)-biphenyl are dissolved in 150 ml of a 1:1 water-/ethanol mixture, the solution is raised to the boil and 9 g of 6-chloro-1-hexanol are slowly added dropwise, whilst stirring, after which the batch is refluxed for about 10 hours. When the reaction solution has cooled, it is acidified with HCl and the product is extracted with CHCl₃ in a separating funnel. The CHCl₃ is then stripped off and the crude product is recrystallized from ethanol (melting point 118° C.).

4.3. 4-[6-(2-Methylpropenoyloxy)-hexoxy]-4'-(2-methylbutoxy)-biphenyl 6.8 g of the biphenyl derivative prepared under 4.2, 10.5 g of methacrylic acid, 0.5 g of p-toluenesulfonic acid and 0.5 g of hydroquinone as an inhibitor are dissolved in 100 ml of CHCl$_3$ and the solution is refluxed for about 20 hours, using a water separator. It is then taken up in 100 ml of ether, washed several times with saturated Na$_2$CO$_3$ solution (until the aqueous phase no longer shows a coloration) and dried with Na$_2$SO$_4$, and the solvent is stripped off. The crude product is recrystallized from ethanol. Phase transitions k 42.5 s 49 i.

4-[6-(Propenoyloxy)-hexoxy]-4'-(2-methylbutoxy)-biphenyl is prepared by a similar method.

The monomers prepared in Examples 1 to 4 were identified by elementary analysis and by IR and NMR spectroscopy.

EXAMPLE 5

This describes the preparation of a cholesteric copolymer of the chiral monomer of the structure

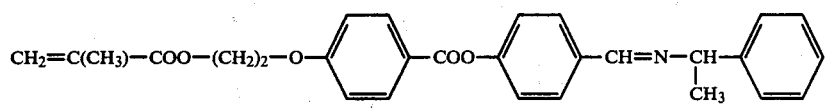

and the nematogenic monomer of the structure

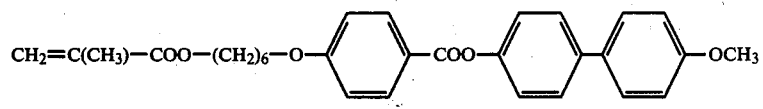

5.1. The two monomers are mass-polymerized by a free radical method. A mixture of the two monomers, containing at most 30 mole % of the chiral monomer, is milled in a ball mill with 1 mole % of azodiisobutyronitrile (AIBN) and is heated, between two small glass plates, oxygen being excluded, at above the melting point of the mixture but always above 55° C. After completion of the polymerization, but no earlier than after 10 minutes, the sample is cooled, whereupon it firmly bonds the two small glass plates to one another. If, in this state, the temperature is raised to above the glass transition temperature of the copolymer, the mesophase region of the copolymer is reached. The substance is liquid-crystalline and the texture or orientation of the molecules can be varied by external factors (temperature, electrical and magnetic fields, and pressure), preferably at a few degrees below the clearing temperature. The orientation produced can be fixed in the glassy state by cooling.

5.2. The chiral monomer and the nematogenic monomer are copolymerized in solution, using a free radical method. Preferably, 10% strength solutions of the monomers in absolute benzene or tetrahydrofuran, containing at most 5% of initiator, are heated in the absence of oxygen for about 20 hours at 55°-60° C.

The copolymer is then precipitated by adding 10 volumes of methanol or acetone per volume of the above solution, and is centrifuged off and dried. The copolymer is purified by reprecipitating it twice.

The copolymer obtained after reprecipitation is amorphous and does not exhibit a liquid-crystalline structure. If, for example, it is introduced between small glass plates, or applied as a film to a support, and heated to above the glass transition temperature but below the clearing temperature, the cholesteric Grandjean texture forms spontaneously. This texture can be fixed in the glassy state of the copolymer by cooling to below the glass transition temperature.

5.3 The text which follows describes the optical properties of four copolymers obtained as described in 5.1. or 5.2., the copolymers differing in respect of the proportion of the chiral component. The wavelength $\lambda_R$ of the reflection of circular-polarized light was determined spectroscopically at a temperature, reduced to the clearing temperature $T_{Cl}$, of $T^* = T_{meas}/T_{Cl} = 0.9$ in the liquid-crystalline phase.

The nature of the circular-polarized light was determined by circular polarization filters. The cholesteric copolymers reflect laevo-circular-polarized light if the chiral component (−)-(1)-phenylethylamine is used in the chiral comonomer.

| $X_{chiral}$ | $T_{Cl}$ (°C.) | $\lambda_R$ nm ($T^* = 0.9$) |
|---|---|---|
| 11 | 245 | 1,260 |
| 17 | 229 | 710 |
| 21 | 216 | 560 |
| 25 | 203 | 465 |

$X_{chiral}$ = mole fraction of the chiral comonomer in the monomer mixture before polymerization.

The measurement of $\lambda_R$ by transmitted light (using a transparent support for the polymer film) gives the half-life of $\lambda_R$ in the above Example in the range of from 80 to 350 nm, depending on the preparation and thickness of the sample measured. The reflecting texture can be fixed in the glassy state by rapidly cooling the sample to below the glass transition temperature of the copolymer.

EXAMPLE 6

A mixture, having induced cholesteric characteristics, of a nematic homopolymer of the structure

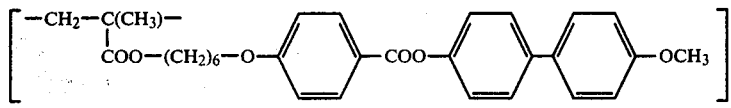

and a chiral homopolymer of the structure

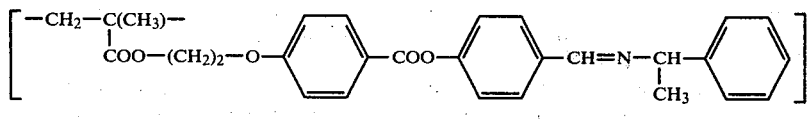

is prepared.

The two homopolymers are prepared from the monomers by free radical mass polymerization or solution polymerization, using similar methods to those described in 5.1. and 5.2.

6.1. The nematogenic monomer is subjected to free radical mass polymerization as follows:

The monomer, mixed with 1 mole percent of azodiisobutyronitrile in a ball mill, is introduced between two glass plates in the absence of oxygen, and is heated to above its melting point (but in any case above 60° C.). On examination under a polarization microscope, it is found after about 3 minutes that the reaction mixture exhibits optically anisotropic, liquid-crystalline properties. As the polymerization progresses, the clear anisotropic substance has hardened after about 10 minutes (the exact time depending on the type of monomer) and firmly bonds the two glass plates together. If, in this state, the temperature is raised to above the glass transition temperature of the homopolymer, the mesophase region of the homopolymer is reached. The substance is liquid-crystalline and the texture and orientation of the molecules can be varied by external factors (electrical and magnetic fields, or pressure). The orientation produced can be fixed in the glassy state by cooling.

6.2. The nematogenic monomer is subjected to free radical solution polymerization. To do so, 1%, 2% or 4% of azodiisobutyronitrile are added to 10% strength solutions of the monomer in absolute benzene and each mixture is heated for 20 hours at 60° C., in the absence of oxygen. The homopolymer is then precipitated from 10 volumes of methanol per volume of benzene solution, and is centrifuged off and dried. The homopolymer is purified by reprecipitating it twice.

If the monomer

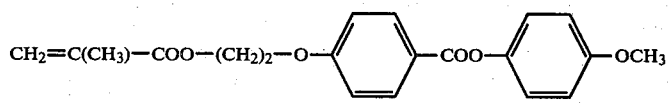

is polymerized by this method, it is found that the mesophase region of the polymers is substantially independent of the initiator concentration, as can also be seen from the tabulation below.

| Initiator | $T_{Cl}$ | $T_g$ |
|---|---|---|
| 1% | 123 | 101 |
| 2% | 122.5 | 98 |

-continued

| Initiator | $T_{Cl}$ | $T_g$ |
|---|---|---|
| 4% | 120 | 96 |

The Table which follows lists the phase transitions of some homopolymers which consist of monomers of the structure $$CH_2=C(R_1)-COO-(CH_2)_n-O-\phi-COO-\phi-R_2$$

| $R_1$ | n | $R_2$ | | | Phase transitions |
|---|---|---|---|---|---|
| CH₃ | 2 | —OCH₃ | g | 100 | n 121 i |
| CH₃ | 6 | —OCH₃ | g | 95 | n 105 i |
| CH₃ | 6 | —CH₃ | g | 75 | n 84 i |
| CH₃ | 2 | —φ—OCH₃ | g | 120 | n 177 i |
| CH₃ | 6 | —φ—OCH₃ | g | 60 | s 133 n 271 i |
| CH₃ | 3 | —φ | g | about 90 | s 176 n 187 i |
| CH₃ | 6 | —φ | g | about 70 | s 164 n 184 i |
| H | 6 | —φ | g | about 70 | s 176 n 191 i |
| CH₃ | 2 | —φ—OC₂H₅ | g | — | s 212 n 300 i |

The phase transitions of the homopolymer obtained from the monomer of the formula

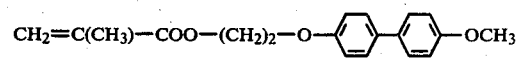

are as follows: g 120 n 150 i

The enthalpies for the phase transition from liquid-crystalline to isotropic were determined by TLC measurement.

The chiral homopolymers shown below and prepared similarly from their monomers exhibit the following properties

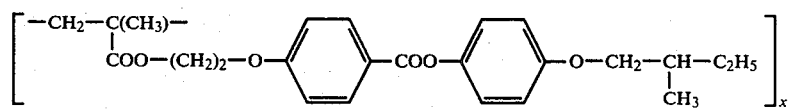

$T_{Cl}$ 140° C. $T_g$ about 95° C. $\Delta H$(cal/g) 2.6 (smectic)

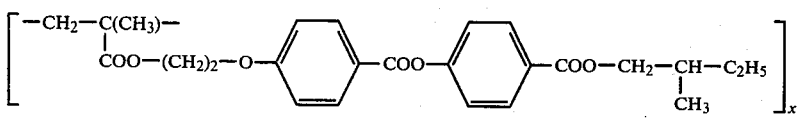

$T_{Cl}-T_g$ about 95° C. ΔH(cal/g)-(isotropic)

6.3. 20 mole% (based on monomer units) of a homopolymer

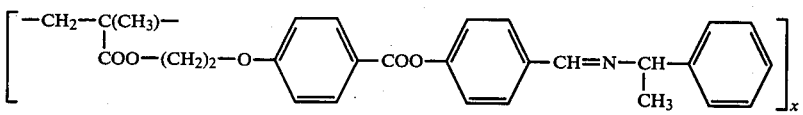

and 80 mole% of a nematic homopolymer

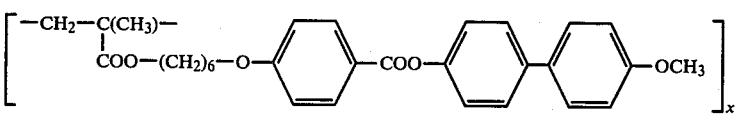

are dissolved in dioxane and the solution is freeze-dried. The solvent-free mixture of the two homopolymers shows a cholesteric Grandjean texture in the liquid-crystalline phase under a polarization microscope.

Using a similar process, cholesteric polymer phases are obtained if low molecular weight chiral compounds are mixed with conventional nematic polymer phases. Preferably, chiral compounds having a molecular structure resembling that of the nematogenic monomer of the particular nematic polymer are employed.

We claim:

1. A composition of matter exhibiting a liquid-crystalline cholesteric polymer phase consisting essentially of (1) at least one copolymer which contains (a) nematogenic units of the formula (I)

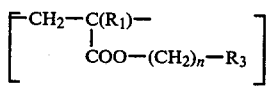

where $R_1$ is hydrogen or methyl, n is an integer from 1 to 6 and $R_3$ is

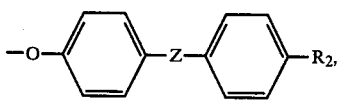

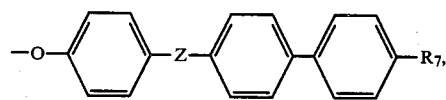

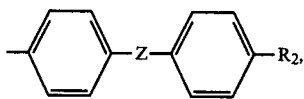

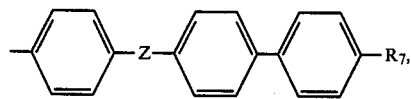

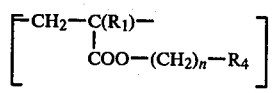

where Z is COO— or OCO—, $R_2$ is —O(CH$_2$)$_m$H, —(CH$_2$)$_m$H or —COO—(CH$_2$)$_m$H, m being an integer from 1 to 6, and $R_7$ is hydrogen or $R_2$, and (b) chiral units of the formula (II)

$$\left[ \begin{array}{c} -CH_2-C(R_1)- \\ | \\ COO-(CH_2)_n-R_4 \end{array} \right] \quad (II)$$

in which $R_1$ is hydrogen or methyl, n is an integer from 1 to 10 and $R_4$ is

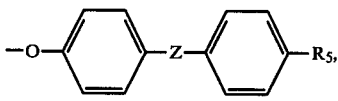

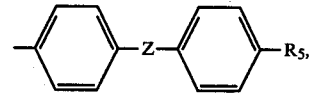

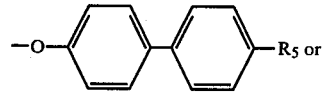

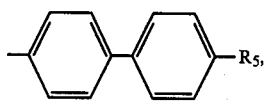

where Z is COO— or OCO— and $R_5$ is —CH=N—$R_6$, —OR$_6$, —COOR$_6$, —CH=CH—COOR$_6$ or —R$_6$, $R_6$ being alkyl or alkylaryl of 4 to 10 carbon atoms and having at least one asymmetric carbon atom or (2) a mixture of (a) a polymer having a nematic structure and containing units of the formula (I) and (b) a compound having a chiral structure.

2. The composition of matter of claim 1, wherein the liquid-crystalline cholesteric polymer phase is a copolymer which contains (a) nematogenic units of the formula (I) and (b) chiral units of the formula (II).

3. The composition of matter of claim 1, wherein the liquid-crystalline cholesteric polymer phase is a mixture of (a) a polymer having a nematic structure and containing units of the formula (I) and (b) a compound having a chiral structure.

4. The composition of matter of claim 3, wherein the compound having a chiral structure is a polymer with chiral units of the formula

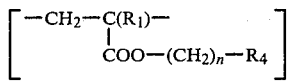

where $R_1$ is hydrogen or methyl, n is an integer from 1 to 10 and $R_4$ is

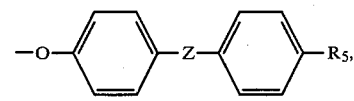

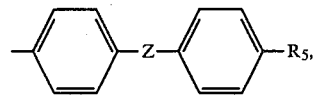

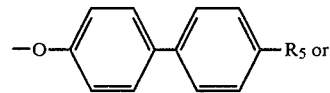

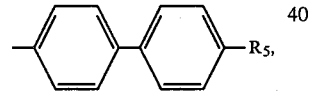

where Z is COO— or OCO— and $R_5$ is —CH=N—$R_6$, —O$R_6$, —COO$R_6$, —CH=CH—COO$R_6$ or —$R_6$, $R_6$ being alkyl or alkylaryl of 4 to 10 carbon atoms and having at least one asymmetric carbon atom.

5. The composition of matter of claim 1, 2 or 3, wherein $R_3$ is

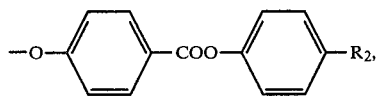

6. The composition of matter of claim 1, 2 or 3, wherein $R_3$ is

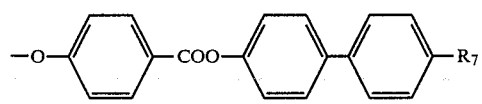

7. The composition of matter of claim 2, wherein $R_4$ is

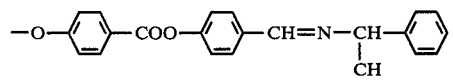

8. The composition of matter of claim 4, wherein $R_4$ is

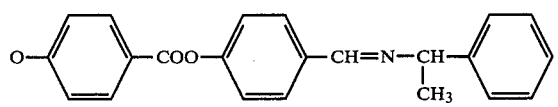

9. The composition of matter of claim 4, wherein $R_4$ is

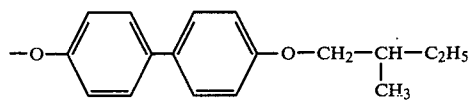

* * * * *

UNITED STATES PATENT AND TRADEMARK OFFICE
CERTIFICATE OF CORRECTION

PATENT NO. : 4,293,435
DATED : October 6, 1981
INVENTOR(S) : Michael Portugall, Heino Finkelmann and Helmut Ringsdorf It is certified that error appears in the above—identified patent and that said Letters Patent is hereby corrected as shown below:

In the formula of claim 7, "$-\underset{\underset{CH}{|}}{CH}-$"

should read -- $-\underset{\underset{CH_3}{|}}{CH}-$ --.

Signed and Sealed this

Ninth Day of March 1982

[SEAL]

Attest:

GERALD J. MOSSINGHOFF

Attesting Officer

Commissioner of Patents and Trademarks